United States Patent [19]
Havira et al.

[11] Patent Number: 5,419,196
[45] Date of Patent: May 30, 1995

[54] ULTRASONIC SIDE-LOOKER FOR RAIL HEAD FLAW DETECTION

[75] Inventors: Robert M. Havira, New Fairfield; Anthony Iorfino, Stamford, both of Conn.

[73] Assignee: Pandrol Jackson Technologies, Inc., Danbury, Conn.

[21] Appl. No.: 34,420

[22] Filed: Mar. 19, 1993

[51] Int. Cl.6 ............................................. G01N 29/04
[52] U.S. Cl. .................................... 73/636; 73/623
[58] Field of Search ................ 73/623, 628, 636, 639

[56] References Cited

U.S. PATENT DOCUMENTS

| | | |
|---|---|---|
| 3,257,843 | 6/1966 | Cowan . |
| 3,937,068 | 2/1976 | Joy . |
| 4,174,636 | 11/1979 | Pagano ............................. 73/636 |
| 4,457,178 | 7/1984 | Turbe . |
| 4,593,569 | 6/1986 | Joy . |
| 4,615,218 | 10/1986 | Pagano . |
| 4,662,224 | 5/1987 | Turbe . |
| 4,689,995 | 9/1987 | Turbe . |
| 4,700,574 | 10/1987 | Turbe . |
| 4,763,526 | 8/1988 | Pagano . |
| 5,020,371 | 6/1991 | Panetti . |

Primary Examiner—Herbert Goldstein
Assistant Examiner—William L. Oen
Attorney, Agent, or Firm—St. Onge Steward Johnston & Reens

[57] ABSTRACT

An ultrasonic rail flaw detection system and technique are described for the detection of flaws in the sides of rail heads. An ultrasonic transducer is oriented, sized, and so-located so as to produce an ultrasonic beam within the head whereby at least a portion of the beam will intersect a lower side corner independent of the curvature of the rail head running surface and the amount of head wear. The presence of premature reflections or the or absence of reflections can be used to detect flaws such as vertical fractures in the rail head. The side-looker is so oriented as to produce a beam in the rail head that lies within 45° to 75° of the normal to the rail surface. The side-looker can further be so located that its beam does not interfere with or be interfered by beams from other transducers used to investigate the rail and mounted in the same wheel assembly as the side-looker.

9 Claims, 4 Drawing Sheets

ULTRASONIC SIDE-LOOKER FOR RAIL HEAD FLAW DETECTION

FIELD OF THE INVENTION

This invention relates to ultrasonic investigations of rails generally and more particularly to a technique for ultrasonically investigating the side of a rail head and other parts of the rail with a plurality of simultaneously operating ultrasonic transducers.

BACKGROUND OF THE INVENTION

Ultrasonic investigation of rails is well known. For example U.S. Pat. No. 4,165,648 describes a wheel assembly, which is adapted to ride on top of a rail and contains a plurality of ultrasonic transducers for investigating different parts of a rail. A pair of transducers are oriented to investigate the rail along opposite longitudinal directions, another transducer is oriented to vertically investigate the web of the rail and a fourth transducer is intended as a side-looker with which side portions of the rail head are to be laterally investigated.

The side-looker is mounted on a yoke assembly, near the axis and is positioned off to one side to investigate an opposite side of the rail head. The transducer produces a beam intended to have a 40 degree angle relative to the normal to the rail surface inside the rail head so that the beam will intersect one of the lower corners of the head. Although this transducer can be effective for detecting vertically split rail heads it does not accommodate the effect of the curvature of the rail head and the head wear that one encounters under field conditions.

The curvature of the rail head causes a variety of angles of both compressional and shear components to be present inside the rail head and thus creates difficulties in interpreting the resulting signals detected at the transducer. For example, if the resultant angle is to be 40 degrees inside the head for a compressional wave, then a 20 degree shear wave will also be present. Since a mode conversion is relied upon to accomplish the resultant angle in the rail head, there is but a limited range of incident angles available inside the wheel. This limitation arises from the use of essentially a common exit point for all of the transducers mounted inside the wheel and the resulting need to avoid interference with the other transducers by internal wheel reflections from the side-looking transducer.

The '648 patent illustrates that for one particular beam direction, the corners of one rail head and its proportionately smaller sizes are likely to be intersected by a 40 degree beam. However, when the rail head undergoes significant wear on its upper surface, as is often the case, the beam will miss the lower corner. Instead the beam is likely to strike an inner surface near the web, which scatters the beam inside the head, and fails to provide the type of return needed to detect vertical flaws near the side of the rail head.

SUMMARY OF THE INVENTION

In a rail flaw detection system, in accordance with the invention, a side-looking transducer is used that is so mounted and located that it produces a beam of shear wave ultrasonic energy at the proper angle inside the rail head to enable detection of vertical flaws near the sides of the head and avoid interference with other transducers in a broad range of field conditions.

This is achieved in accordance with one form of the invention by placing a side-looking transducer on a conventional yoke within a rotating fluid-filled wheel in such a manner that the transducer produces a beam from a location near the peripheral part of the wheel. The incident beam angle within the wheel, as measured relative to the normal at the wheel surface, and the beam's width are further selected so that the ultrasonic illumination inside the rail head is sufficiently wide to generate returns that can identify the presence of vertical fractures despite significant rail head distortions and wear.

For example, in accordance with one form of the invention, a side-looking transducer is mounted below the yoke and has an orientation that is selected to produce an ultrasonic beam within the rail head that is in the range from about 45° to about 75° relative to the normal at the surface as measured in a plane that is transverse to the running surface of the rail. The beam further has a width sufficient so that at least a portion illuminates one of the lower corners of the rail head despite the presence of extensive head wear and causes an acoustic return from which the presence of a vertical flaw can be detected.

With a side-looking transducer in accordance with the invention, rail head defects can be detected by way of an interruption of the beam reflecting from the lower corner as lack of an expected response. Alternatively, the defect can be detected from a positive reflection from the flaw itself. Each detection tends to occur at a different time and so may be utilized to ascertain the presence of a flaw.

The positioning of the side-looking transducer is selected to avoid interference with the operation of other transducers as are typically employed with a yoke inside the wheel to investigate the head and web of a rail forwardly, downwardly, and rearwardly from the wheel. Hence, an independent flaw detection wheel for the side-looker is not needed, though one could employ one.

It is, therefore, an object of the invention to provide an apparatus and method for the detection of flaws in the side portions of the head of a rail. It is a further object of the invention to provide an improvement to an ultrasonic rail investigating apparatus whereby it can, in addition to longitudinal and downward investigations of a rail, detect the presence of flaws in a side of the rail head.

These and other objects and advantages of the invention can be understood from the following detailed description of an embodiment as illustrated in the drawings.

DETAILED DESCRIPTION OF DRAWINGS

Figure 1:
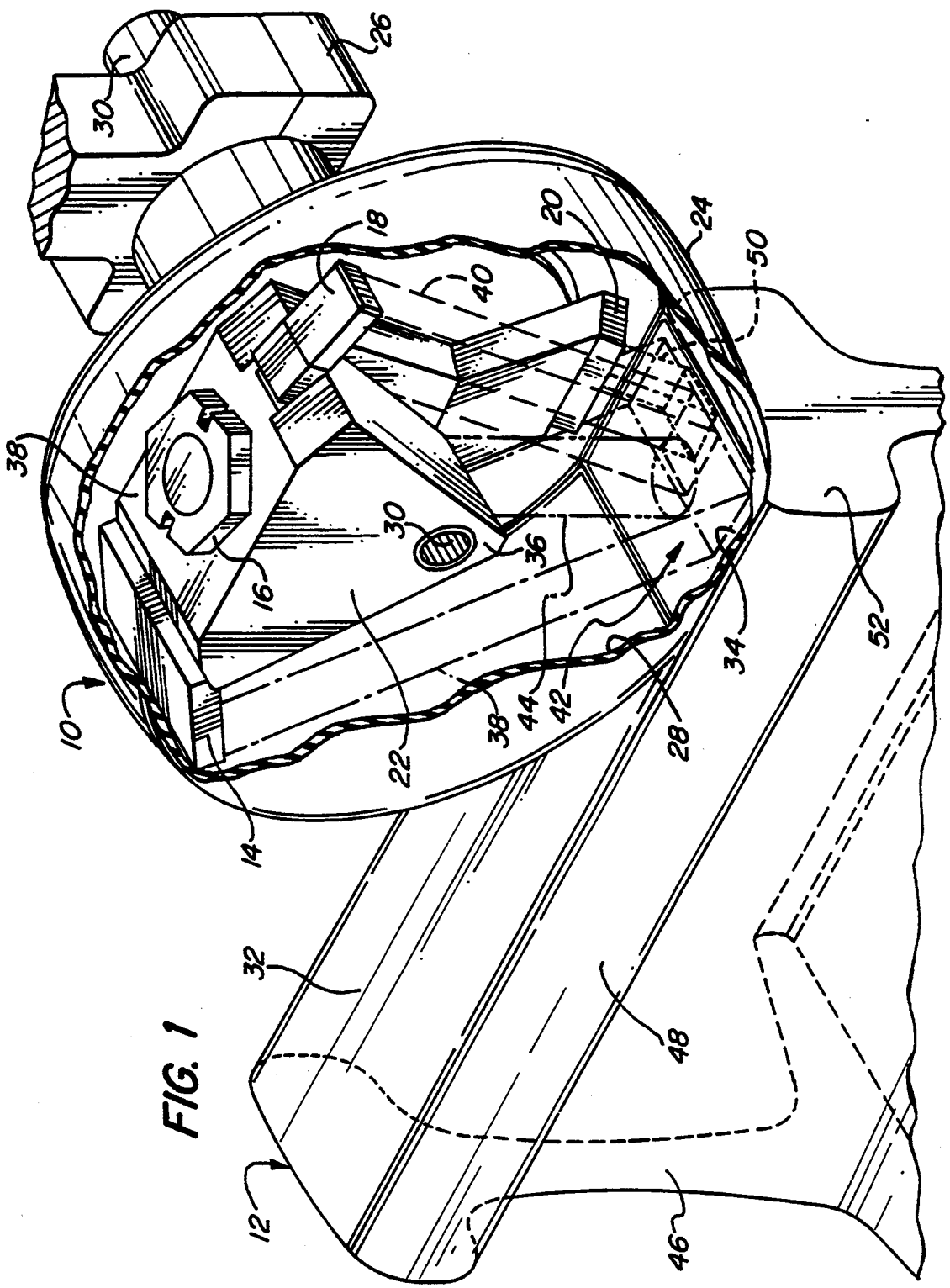
FIG. 1 is a perspective broken away view of an ultrasonic rail investigating wheel using a side-looking transducer in accordance with the invention.

With reference to FIG. 1, a wheel-type ultrasonic investigation apparatus 10 for ultrasonic inspection of a rail 12. The apparatus 10 is part of a flaw detection system (not shown) that is mounted on a carriage and includes suitable electronic signal processing equipment to analyze the return signals detected by ultrasonic transducers 14, 16, 18, and 20 mounted to a yoke 22 inside a rotating fluid-filled wheel 24.

The wheel 24 is rotationally mounted to a support 26 of the carriage which is not shown. Typically, four wheels 24 are used, two for each rail 12. Each wheel 24 is filled with a fluid mixture of glycol and water to improve the ultrasonic coupling through the flexible outer membrane 28. The yoke 22 is affixed to twin axially-aligned but spaced-apart shafts 30 and is held in a fixed stable position as illustrated while the wheel membrane 28 rotates as it travels along the top surface 32 of rail 12. Suitable downward pressure is applied to the wheel 24 to produce a flat spot 34 in membrane 28 for appropriate ultra-sonic transmission into and out of the rail 12.

Yoke 22 has a generally triangular shape and is oriented so that its apex 36 faces downwardly and is below shaft 30. The base portion 38 of yoke 22 supports the three transducers 14, 16, and 18. Transducers 14 and 18 produce ultrasonic beams 38, 40 respectively, each of which is directed at a generally common exit area 42 at the wheel flat 34. Transducer 16 is oriented to produce a vertical ultrasonic beam 44 that extends through a bore, not shown, in yoke 22 and is also incident onto the area 42. Beams 40 and 44 are intended to investigate the web 46 of rail 12. Transducers 14, 18 produce beams in opposite longitudinal directions to investigate the rail head 48 and web 46 respectively in a manner that is known in the art.

Transducer 20 is a side-looking transducer and is mounted well below the apex 36 of yoke 22 and to its side. Transducer 20 produces an ultrasonic beam 50 that is also incident on flat 34, but in a lateral direction to investigate the side 52 of rail head 48.

All transducers 14, 16, 18, and 20 operate in both a transmit and receive mode and usually simultaneously but can be operated separately.

Figure 2:
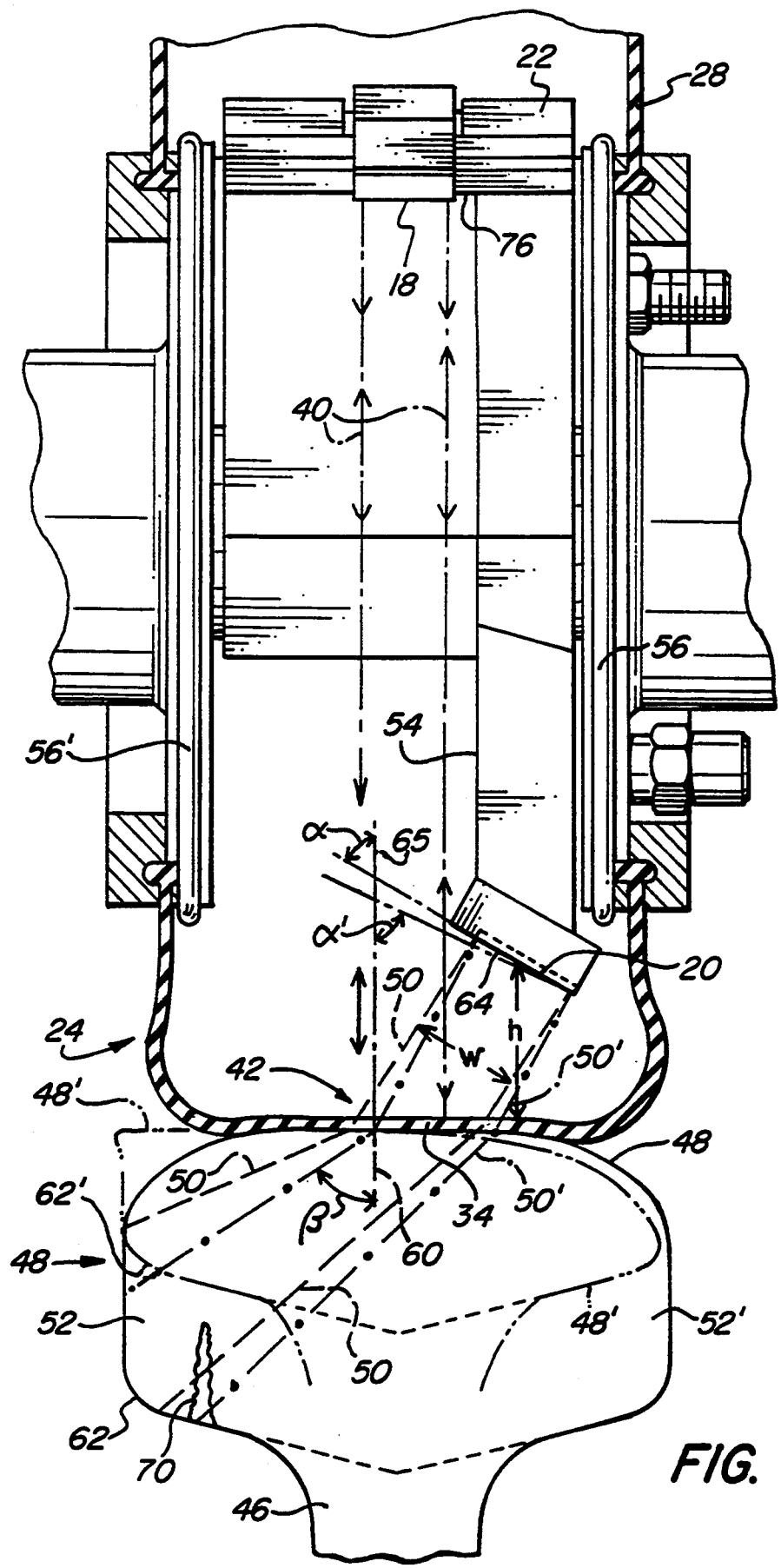
FIG. 2 is an end-on elevation view of the rail investigating wheel illustrated in FIG. 1.
Figure 3:
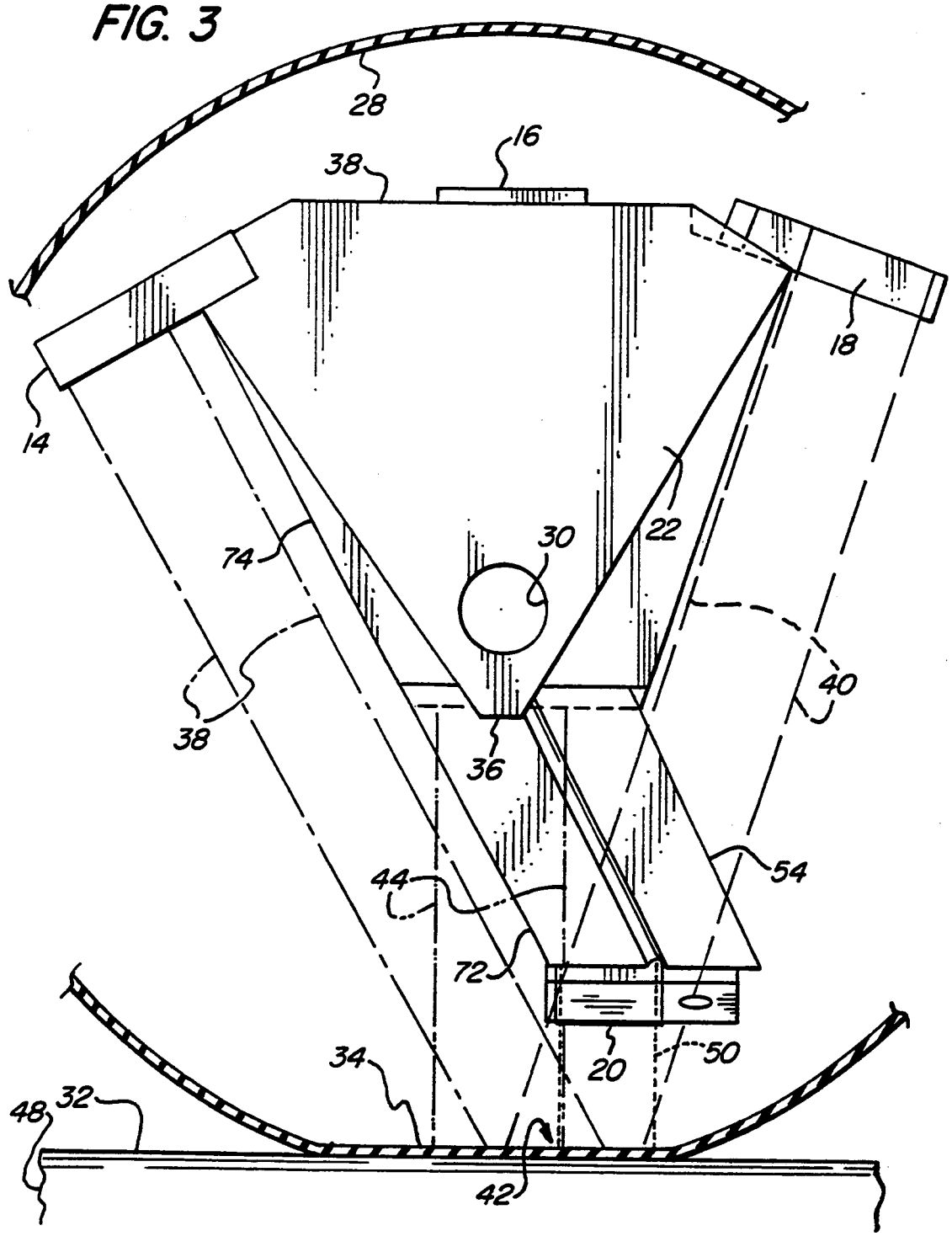
FIG. 3 is a side view in elevation of the yoke and side-looker transducer as shown in FIG. 2.
Figure 4:
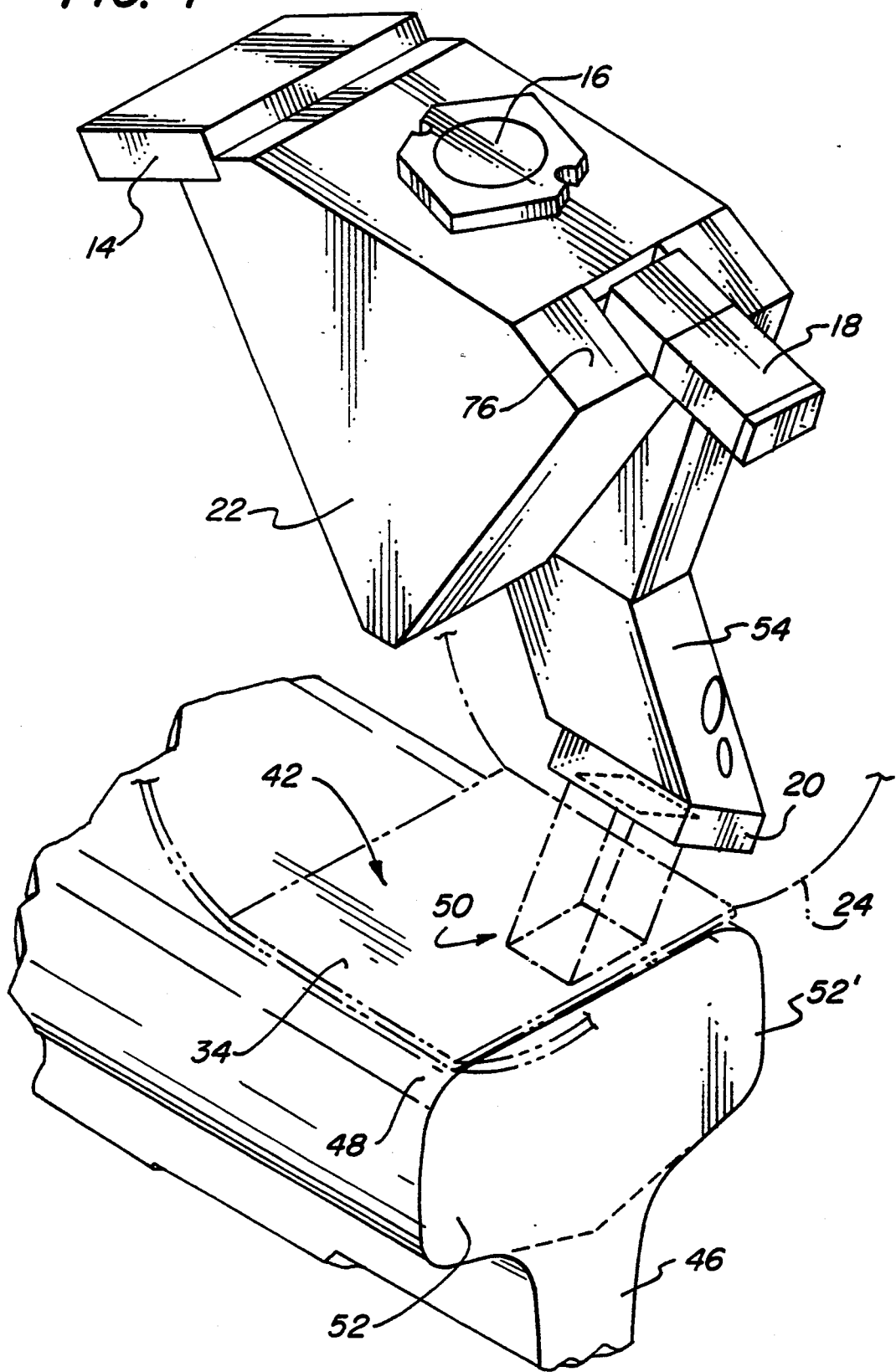
FIG. 4 is a perspective view of a yoke and side-looker transducer as used in the embodiment of FIG. 1.

The side-looking transducer 20 is mounted to yoke 22 by way of a removable extension bracket 54. Alternately, yoke 22 can be formed so as to have an extension 54 become an integral part. With reference to FIGS. 2, 3, and 4, the side-looker 20 is suspended to just below an adjacent side flange 56, to a region that is near the flat portion 34 of the flexible outer wheel membrane 28, but not so close as to be interfered with from wheel vibration or bouncing effects attributable to irregularities encountered along the running top surface 32 of rail 12. By making wheel 10 wider in its axial dimension, transducer 20 can be raised along the beam 50 and moved more to the axis 30 without interference with the other beams. If the side-looking transducer 20 is mounted on a yoke in a separate wheel, the side-looker can be located anywhere along beam 50.

The side-looker 20 further is inclined relative to the central vertical 60 to rail 12 to form an angle, alpha. The angle alpha is selected so as to provide an optimum beam inside rail 12 for inspection of side 52 and assure that at least a portion of the beam 50 will intersect the lower corner 62 of rail head 48. The side-looker 20 further is so sized as to produce a sufficient beam width W within the rail head 48 to assure intersection of lower side corner 62 even when a substantial amount of the upper part of the rail head 48 has been worn away as illustrated in FIG. 2 for a rail head 48'.

Side-looker 20 preferably employs a rectangular ultrasonic transducer whose outer emitting surface 64 is generally flat. The orientation of the side-looker 20 is such that it produces within rail head 48 a beam whose directions are within a head angle beta within the range from about 45° to 75° to the normal at the rail surface 32 as measured in the plane of FIG. 2 that is transverse to the running surface 32. This head angle is a function of conditions such as the orientation of surface 32 relative to central normal 60, the nature of the liquid employed inside wheel 24 and thus the velocity of the beam inside the liquid, the material of which the flexible wheel 24 is made and the curvature, if any, of the rail surface 32.

In order to assure a reflection from lower side corner 62, the available range of angle for the orientation angle alpha of side-looker emitting surface 64 is generally from about 61° to 65.50°, though some variations from that may be used to adjust for variations in the other conditions set forth above. The angle alpha is measured relative to the vertical orientation of wheel 10 and yoke 22. Typically, the vertical lies in a plane that is perpendicular to the axis of rotation of wheel 10 and thus also shafts 30. The vertical 65 is aligned with the central axis of web 46 and at the center of the rail surface 32 tends to be coincident with the center normal 60. When surface 32 is distorted due to wear as for rail head 48' in FIG. 2, the normal 60 to the surface is no longer aligned with vertical 65.

In the view of FIG. 2, two ultrasonic beams 50 and 50' are shown, corresponding to alpha angles of 65.5° and 61° respectively. Each beam is substantially parallel within the fluid-filled wheel 24 but diverges once a mode conversion at the surface 32 of rail 12 has taken place primarily due to the curved shape of the rail head surface 32. The beam 50 is incident on that portion of the rail head that lies primarily to the side where the side-looker 20 is located. In FIG. 2, that is primarily on the right half relative to the center normal 60. The beam typically is of the order of about 0.5 inches square. The height h, as measured from the center of transducer 20 to the surface 32 of rail 12, is selected to avoid interference with beams such as 38 while being able to illuminate the rail head 48 with the desired beam angle and beam width.

Within the rail head 48, the beam 50 is diffracted with a beam angle in the range from about 45° to 67° relative to the normal at the rail surface and is sufficiently wide to assure incidence on lower side corner 62 and cause a reflection for most applications.

In the event that a vertical flaw, such as 70, is present, the reflections from the corner 62 are interrupted and this can be detected from a lack of an expected return, or from a premature return as obtained from the signals outputted by side-looker 20. Signal processing techniques to do so are well known in the art.

With reference to FIG. 2 and 3, the shape and orientation of the extension 54 can be appreciated. In FIG. 3, the transducer 14 produces an ultrasonic beam 38 that remains substantially straight with little divergence. Extension 54 is so shaped that its side surface 72 is parallel to beam 38 and in essence a straight continuation of side 74 of the triangularly-shaped yoke 22. In this manner, interference by side-looker 20 with beam 38 is avoided. The extension 54 further is sized to place the side-looker substantially to one longitudinal side, as viewed in FIG. 3, of the vertical centrally-located web investigating beam 44. As a result, extension 54 takes the side-looker 20 away from beam 44 generated by transducer 16, so that interference with and from that beam is avoided.

With reference to FIG. 2 transducer 18 is mounted centrally with respect to yoke 22. Hence, by mounting the side-looker 20 to the side of yoke 22, interference with beam 40 is avoided.

Hence, with a side-looking transducer in accordance with the invention side portions of rail heads can be reliably investigated for defects including vertical flaws. A side-looker of this invention can be conveniently assembled with a conventional rail wheel investigating assembly without causing interference with beams from other transducers. However, a side-looking transducer of this invention can be used alone in a wheel. Both sides of a rail head can be investigated by placing one side-looking transducer in each of the two wheels traveling over the same rail but arranged to investigate laterally opposite sides 52 and 52' of the rail head 48. Each side-looker can be mounted in its own separate wheel or two, side-lookers, which are oriented to investigate opposite sides of a rail head, can be mounted in one separate wheel.

Having thus described one embodiment in accordance with the invention, its advantages can be appreciated. Variations can be made without departing from the scope of the invention.

What is claimed is:

1. In an apparatus for an acoustic investigation of a rail with a fluid filled rotating wheel inside of which is a stable yoke on which a plurality of ultrasonic transducers are mounted for the investigation of the rail with ultrasonic beams that exit at a generally common flat area formed in a flexible outer membrane of the wheel as it rotates about an axis to travel along the top running surface of the rail head of the rail under inspection and wherein the beams have different angles relative to the normal to the top running surface to investigate forward, backward and downward regions of the rail, the improvement comprising:

an ultrasonic side-looking transducer mounted to the yoke and located in the vicinity of the generally common flat area below and on a side of the yoke, said side-looking transducer being oriented so as to produce an ultrasonic beam within the wheel fluid that is directed at the common flat area with a fluid angle within a range from about 61 degrees to about 65.5 degrees relative to a normal to the top surface of the rail, with the normal located in a plane which is transverse to the rotational axis of the wheel, so as to produce a beam inside the rail head with a head angle relative to the normal in the range from about 45 degrees to about 75 degrees as measured within a plane that is generally transverse to the top running surface of the rail, said beam further having a width selected to produce, within the rail head, an ultrasonic beam, at least a portion of which remains incident on a lower corner thereof independent of the presence of significant rail head wear and produces reflections from the lower corner; said reflections or an absence thereof being able to indicate the presence of vertical rail head flaws which run generally along the running surface of the rail.

2. The improved rail investigation apparatus as claimed in claim 1 wherein said yoke is generally triangularly shaped and is mounted with an apex facing downward when in operation, said yoke having an extension extending from a side of said yoke and having a lower end to which the side-looking transducer is mounted, said extension being sized so as to locate said side-looking transducer below the apex of said yoke and below said axis.

3. The improved rail investigating apparatus as claimed in claim 2 wherein said yoke has a central bore extending therethrough in general alignment with said flat area of the wheel to investigate the web of the rail, said yoke having an upper located base extending forwardly and rearwardly of the axis, with transducers which are aligned with said forward and rearward looking beams being mounted respectively to the rearward and forward parts of the yoke base to direct ultrasonic beams generally parallel to sides of the yoke onto said flat area and investigating the head and web of the rail in opposite directions, and a web investigating transducer mounted to the yoke base so as to direct an ultrasonic beam through said bore onto the flat area of the wheel, wherein said extension is further so shaped so as to locate the side-looking transducer to one side of the axis of rotation of the wheel and substantially to one longitudinal side of the ultrasonic beam from said web investigating transducer.

4. The improved rail investigating apparatus as claimed in claim 2 wherein said wheel has a pair of side located circular flanges to which said flexible membrane is attached, said side-looking transducer being located adjacent a peripheral edge of one of said flanges.

5. The improved rail investigating apparatus as claimed in claim 3 wherein said extension is shaped so that a side thereof is substantially parallel to an ultrasonic beam from one of said transducers mounted to the base of the yoke.

6. A side-looking ultrasonic transducer for use in an ultrasonic investigation with a fluid wheel assembly in which the side-looking transducer is mounted to a yoke to enable an acoustic investigation of the side of a rail head as the wheel travels along an upper running surface of the rail, comprising:

an ultrasonic side-looking transducer having an emitting surface, means for mounting the side-looking transducer to the yoke and positioning the transducer in the vicinity of the upper running surface so as to be able to inject an ultrasonic beam into a side of the rail head and receive and detect reflections from a lower side corner thereof, said emitting surface being so sized and oriented relative to a normal to the running surface of the rail head so as to form a fluid angle with said normal that is within the range from about 61° to about 65.5° to produce a beam angle within said rail head relative to the normal that is within the range from about 45° to about 75° degrees and is sufficient to obtain reflections from said lower side corner substantially independent from the curvature and wear of the upper running surface of the rail.

7. The side-looking ultrasonic transducer as claimed in claim 6 wherein said wheel assembly includes side-located annular flanges and a flexible ultrasonically transparent membrane enclosing, with said flanges, the yoke and side-looking transducer; and wherein said mounting means positions the side-looking transducer in the vicinity of the periphery of a said flange and to one side of the yoke.

8. A method for acoustically investigating the head of a rail for defects in the side thereof comprising the steps of:

placing an ultrasonic transducer on a yoke within a fluid-filled wheel near the top surface of the rail;

activating the transducer to cause a beam of ultrasonic energy to be directed towards a flat spot of the wheel where it makes contact with the top surface of the rail during wheel travel over the rail;

directing the beam of ultrasonic energy at a fluid angle which is in the range from about 61 degrees to about 65.5 degrees relative to a normal to the top surface of the rail so as to inject an ultrasonic beam that has a head angle inside the rail head within the range from about 45° to about 75° relative to the normal sufficient to intersect a lower side corner of the rail head substantially independently of extensive wear of the rail head.

9. The method as claimed in claim 8 wherein the transducer is activated at a location selected to inject the ultrasonic beam primarily at one side of the rail head so as to be able to be incident upon said lower side corner in an opposite side of the rail head.

* * * * *